United States Patent [19]

Laber et al.

[11] 4,049,817
[45] Sept. 20, 1977

[54] SYNERGISTIC COMPOSITIONS

[75] Inventors: Georg Laber; Eberhard Schutze, both of Vienna, Austria

[73] Assignee: Sandoz Ltd., Basel, Switzerland

[21] Appl. No.: 674,387

[22] Filed: Apr. 7, 1976

Related U.S. Application Data

[63] Continuation-in-part of Ser. No. 547,546, Feb. 6, 1975, abandoned, which is a continuation-in-part of Ser. No. 386,847, Aug. 8, 1973, abandoned.

[30] Foreign Application Priority Data

Aug. 14, 1972 Switzerland ............... 12008/72

[51] Int. Cl.$^2$ ............................................. A61K 31/425
[52] U.S. Cl. ........................................ 424/270; 424/272
[58] Field of Search ............................... 424/270, 272

[56] References Cited

PUBLICATIONS

Chemical Abstracts 63:2149d (1965).
Chemical Abstracts 66:1364a (1967).
The Merck Index, 8th Ed., Merck & Co., Inc., Rahway, N. J., 1968, p. 475.

*Primary Examiner*—Jerome D. Goldberg
*Attorney, Agent, or Firm*—Gerald D. Sharkin; Robert S. Honor; Timothy G. Rothwell

[57] ABSTRACT

The invention provides synergistic compositions comprising a benzisothiazolinone derivative and a 2-nitrofuryl or 2-nitrothienyl derivative. The compositions are useful as antimicrobial agents.

4 Claims, No Drawings

SYNERGISTIC COMPOSITIONS

This application is a continuation-in-part of our copending application Ser. No. 547,546 filed Feb. 6, 1975 now abandoned which is a continuation in part of out copending application Ser. No. 386,847 filed Aug. 8, 1973 now abandoned.

The present invention relates to pharmaceutical compositions.

More particularly, the present invention provides a composition comprising a compound of formula I,

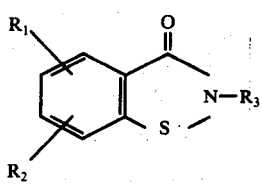

in which
$R_1$ and $R_2$ are the same or different and each signifies hydrogen, lower alkyl, lower alkoxy, nitro, amino, carboxylic acid amide or hydrogen, and
$R_3$ is hydrogen, aminoalkyl, dialkylaminoalkyl, hydroxyalkyl, alkoxyalkyl, cycloalkyl, benzyl or phenethyl, provided that at least one of $R_1$, $R_2$ and $R_3$ is other than hydrogen,
and a compound of formula II,

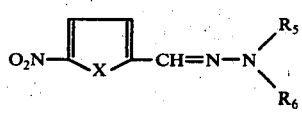

in which either $R_5$ signifies hydrogen, and $R_6$ is a radical of formula III,

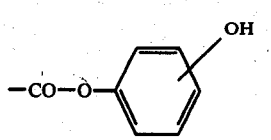

or $R_5$ and $R_6$, together with the nitrogen atom to which they are attached, form a heterocyclic radical having 5 to 6 ring members, which may contain one or more further hetero atoms selected from sulphur, nitrogen and oxygen, and which is unsubstituted or substituted by nitro, amino, oxo, hydroxy or lower alkyl, and X signifies oxygen or sulphur, the compound I being present in an amount of from 10 to 90%, and the compound II in an amount of from 90 to 10%, based on the total weight of compounds I and II.

The compounds of formula I are known and exhibit a growth-inhibiting or destructive effect towards a wide spectrum of micro-organisms, such as bacteria, fungi and protozoa, in particular Staph. aureus, E. coli or Proteus vulgaris. They are therefore indicated for use as locally effective antimicrobial agents and are also suited for topical use, e.g. in the form of ointments, powders for strewing or tinctures.

Compounds of formula II are also known or may be prepared in conventional manner from available starting materials, for example as described in Examples 6 and 7, hereinafter. The antibacterial effect of such known compounds has also been described in the literature.

The present invention is based on the finding that the combination of the compounds I and II exhibits an effect which is surprisingly considerably superior to the sum of the effects of the individual components.

Suitable compounds of formula I include those in which $R_2$ is hydrogen, particularly those of formula Ia,

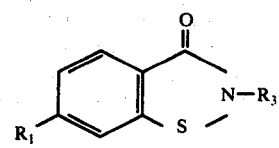

in which $R_1$ and $R_3$ are as defined above, more particularly those of formula Ib,

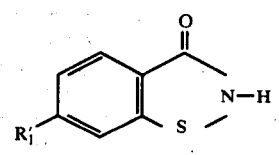

in which $R_1'$ has the same significance as $R_1$, defined above, except that it may not be hydrogen.

$R_1$ and $R_1'$ suitably signify halogen, lower alkyl, lower alkoxy, nitro or amino, more suitably halogen, lower alkyl or lower alkoxy, particularly halogen.

The most preferred compound of formula I is 6-chlorobenzisothiazolinone.

The preferred compounds of formula II include those of formula IIa,

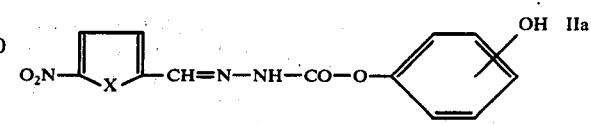

in which X is as defined above, and, more preferably, those of formula IIb,

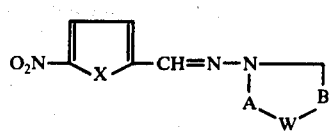

in which
A and B, which may be the same or different, each signifies —CH$_2$— or

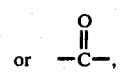

W signifies oxygen, sulphur or imino, and
X is as defined above.
W preferably signifies oxygen or imino, more preferably oxygen. X preferably signifies oxygen.

The most preferred compound of formula II is 3-[(5-nitrofurfuryliden)amino]-2-oxazolidinone. (Furazolidone).

The compounds of formula I may be employed in free base form or in the form of pharmaceutically acceptable acid addition salts. Suitable such acid addition salts include organic acid salts, such as the fumarate, tartrate, or benzene sulphonate, and mineral acid salts, such as the hydrochloride, hydrobromide or sulphate.

As used in the above formulae, "alkyl" or "alkoxy" when present as a substituent or as part of a substituent, are preferably lower alkyl or alkoxy. Preferred lower alkyl or alkoxy radicals contain 1 to 6, in particular 1 to 4 carbon atoms. "Halogen" is preferably chlorine or bromine. Suitable cycloalkyl radicals contain 5 to 8, preferably 5 or 6 ring carbon atoms.

The compositions of the invention preferably comprise the compound of formula I in an amount of from 15 to 85, particularly 20 to 80, more preferably 20 to 35%, in particular about 25%, and the compound of formula II in an amount of from 85 to 15, particularly 80 to 20, more preferably 80 to 65%, in particular about 75%, the percentages being based on the total weight of the compounds I and II.

As mentioned, the combinations of the compounds I and II, exhibits an effect surprisingly superior to the sum of the effect of the individual components. This may be shown in conventional manner. For example, the minimum inhibiting concentration of each of the separate components may routinely be determined by using the series dilution test. The minimum inhibiting concentration of each component may then be redetermined in the presence of various concentrations of the other component. The results may then be treated graphically in accordance with Lowe's method (isobol diagram), Die Antibiotika, *I* (1), 65- [1962].

The compositions of the invention may be formulated in conventional manner and may include conventional inorganic or organic, pharmaceutically acceptable diluents or carriers, and, optionally, other excipients, and may also include other pharmacologically active adjuvants not materially adversely affecting the effect of the main active agents. The compositions may suitably be administered in such forms as tablets, capsules, powders, granulates, solutions or suspensions.

Inert adjuvants or additives which may be admixed with the compositions include sweetening agents, flavouring, colouring and preserving agents, fillers and carrier materials, for example diluents such as calcium carbonate, sodium carbonate, lactose, polyvinyl pyrrolidone, mannitol or talc, granulating and disintegrating agents, such as starch or alginic acid, binding agents such as starch, gelatin or acacia, and lubricants such as magnesium stearate, stearic acid or talc. Preparations for oral administration may contain the usual suspending agents, e.g. methyl cellulose, tragacanth or sodium alginate. Examples of suitable wetting agents which may be used are: lecithin, polyoxyethylene stearate or polyoxyethylene sorbitan monooleate. Ethyl-o-hydroxybenzoate may, for example, be used as preserving agent. Examples of diluents which may be used in solid compositions, e.g. for the production of capsules are: calcium carbonate, calcium phosphate and kaolin.

The compositions of the invention are indicated for use in the treatment of microorganism infections in humans and in domestic animals, e.g. pigs or calves, in particular in infections of the gastrointestinal tract and other local infections in the organism. For such use, the dosage administered will, of course, vary depending on the composition, mode of administration and treatment desired. However, in general, satisfactory results are obtained when administered at a daily dosage of from about 100 to 500 mg/kg of animal body weight, conveniently given as a single dose or in divided doses two to five times daily. For the larger mammals, the total daily dosage is from about 3 to 15 g and dosage forms suitable for oral administration comprise from about 600 mg to 7.5 g of the composition admixed with a solid or liquid pharmaceutical diluent or carrier.

In the case of treatment of domestic animals, the compositions may suitably be administered with feedstuff or drinking water. The dosage will of course vary depending on the size and age of the animal and the effect desired. An indicated suitable unit dose for calves is from about 4 to 6 g and for young to medium pigs, from about 500 mg to 5 g. Such unit does may suitably be administered 1 to 3 times daily.

The following Examples illustrate the invention.

EXAMPLE 1

Production of an active agent granulate by spray drying

Composition of the starting mixture:

| | |
|---|---|
| 6-chlorobenzisothiazolinone | 60 g |
| 3-[(5-nitrofurfurylidene)amino]-2-oxazolidinone | 180 g |
| bismuth subcarbonate | 1200 g |
| polyvinyl pyrrolidone | 120 g |
| mannitol | 1437 g |
| trisodium citrate (5½ $H_2O$) | 3 g |
| total amount | 3000 g |

The mannitol and the trisodium citrate are dissolved in 4 liters of water, and the solution is heated to 50° C. The remaining components are then weighed, thoroughly mixed together and gradually added to the above solution. The resulting mixture is then homogenized in a homogenizer. If necessary, a further amount of water up to a total amount of 7 liters is added during homogenization, whereby subsequently 500 cc of water are used to rinse out the homogenizer. The resulting homogenized material is then spray-dried in the usual manner under a pressure of 4 atmospheres, whereby the temperature of admission amounts to 170° C and the temperature of discharge to 85°–90° C. The resulting spray-dried preparation is moistened with 50% ethanol, pressed through a sieve DIN No. 7 and dried in a drying chamber at 43° C.

EXAMPLE 2

Production of an active agent granulate by spray granulation

Composition of the mixture:

| | |
|---|---|
| trisodium citrate | 30 g |
| water | 300 cc |
| bismuth subcarbonate | 6000 g |
| polyvinyl pyrrolidone | 600 g |
| water | 3000 cc |
| 6-chlorobenzisothiazolinone | 300 g |
| 3-[(5-nitrofurfurylidene)amino]-2-oxazolidinone | 900 g |
| mannitol | 7170 g |
| total amount | 15000 g dry substance |

The trisodium citrate is first dissolved in 300 cc of water, whereupon the bismuth subcarbonate is placed in the bucket of the spray granulator and is sprayed with the sodium citrate solution and spray-granulated. The temperature of the spray granulator amounts to 40°–45°

C, the spraying time of the sodium citrate solution 6 minutes. Drying is then effected for 4 minutes. The sieved mannitol is subsequently placed into the bucket of the spray granulator and the whole material is thoroughly mixed. The corresponding amount of polyvinyl pyrrolidone is subsequently dissolved in 3000 cc of water, and the 3-[(5-nitrofurfurylidene)amino]-2-oxazolidinone as well as the 6-chlorobenzisothiazolinone are suspended therein. The resulting suspension is again spray-granulated with the mixture in the spray granulator. Half of the above suspension is first sprayed into this mixture within 25 minutes, whereupon the apparatus is turned off and the precipitate on the wall of the granulator is scratched off. Spraying is subsequently continued for 25 minutes while adding the second half of the suspension. Rinsing out is then effected with 500 cc of water. The resulting product is then dried at the above temperature for 35 minutes, whereupon the temperature is increased to 60° C and drying is terminated over a further 6 minutes. The resulting granulate is usually very fine-grained. It is rapidly sprayed with a total of 3 liters of water and then dried at 60° C. Sifting is then effected with a DIN sieve No. 7.

EXAMPLE 3

Production of a tablet

Composition of the tablet mixture:

| | |
|---|---|
| 6-chlorobenzisothiazolinone | 10 g |
| 3-[(5-nitrofurfurylidene)amino]-2-oxazolidinone | 30 g |
| bismuth subcarbonate | 200 g |
| polyvinyl pyrrolidone | 20 g |
| mannitol | 240 g |
| Polyclar (high molecular weight polyvinyl pyrrolidone) | 5 g |
| magnesium stearate | 5 g |
| total amount | 510 g |

The first five ingredients are spray-granulated in a granulator as described in Example 2. The resulting granulate is dried, whereupon the Polyclar and magnesium stearate are added to the resulting powder, the mixture is homogenized in a mixer and pressed into tablets in a press.

The 3-[(5-nitrofurfurylidene)amino]-2-oxazolidinone is preferably used in hydrochloride salt form.

EXAMPLE 4

The compositions of the preceding Examples 1 to 3, may be reformulated using, in place of the 6-chlorobenzisothiazolinone, 6-bromo-, 6-methoxy- or 6-methylbenzisothiazolinone.

EXAMPLE 5

The compositions of Examples 1 to 4, may be reformulated using, in place of the 3-[(5-nitrofurfuryliden)amino]-2-oxazolidone,
  1-[(5-nitrofurfuryliden)amino]-hydantoin,
  1-[(5-nitrofurfuryliden)amino]-2-imidazolinone,
  β-(5-nitrofurfuryliden)carbazinic acid (3-hydroxyphenyl) ester,
  or β-(5-nitrofurfuryliden)carbazinic acid (2-hydroxyphenyl) ester.

Production of Compounds of formula IIa

EXAMPLE 6

β-(5-nitrofurfurylidene) carbazinic acid (3-hydroxyphenyl) ester

A solution of 1.7 g of 5-nitrofuran-2-aldehyde in ethanol is added to 2.0 g of carbazinic acid (3-hydroxyphenyl) ester in ethanol/water, and the mixture is heated to 50°14 60° for one hour. After concentration, yellow crystals having a M.P. of 158°–160° C (decomp.), are obtained.

The following compound (Example 7) may be obtained in manner analogous to that described in Example 6, using approximately equivalent amounts.

EXAMPLE 7

β-(5-nitrofurfurylidene) carbazinic acid (2-hydroxypheny) ester

Light yellow crystals having a M.P. of 170°–180° C (decomp.).

We claim:
1. A pharmaceutical composition which comprises 6-chlorobenzisothiazolinone in free base or pharmaceutically acceptable acid addition salt form and 3-[(5-nitrofurfuryliden)amino]-2-oxazolidinone in free base or pharmaceutically acceptable acid addition salt form as the active ingredients, the 6-chlorobenzisothiazolinone being present in an amount of from 20 to 80%, and the 3-[(5-nitrofurfuryliden)amino]-2-oxazolidinone in an amount of from 80 to 20% based on the total weight of active ingredients.

2. A method of combatting microorganisms selected from the group consisting of bacteria, fungi and protozoa in mammals comprising administering to a mammal in need of said treatment, an effective anti-bacterial, anti-fungal or anti-protozoal amount of a composition according to claim 1.

3. A method according to claim 2, in which the microorganism is Staph. aureus, E. coli or Proteus vulgaris.

4. A method according to claim 2, in which the microorganism is Staph. aureus or E. coli.

* * * * *